US006818247B1

(12) United States Patent
Chen et al.

(10) Patent No.: US 6,818,247 B1
(45) Date of Patent: Nov. 16, 2004

(54) ETHYLENE VINYL ALCOHOL-DIMETHYL ACETAMIDE COMPOSITION AND A METHOD OF COATING A STENT

(75) Inventors: Yung-Ming Chen, Cupertino, CA (US); Syed F. A. Hossainy, Fremont, CA (US); Deborra Sanders Millare, San Jose, CA (US); Wouter E. Roorda, Palo Alto, CA (US); Ashok A. Shah, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 216 days.

(21) Appl. No.: 09/844,522

(22) Filed: Apr. 27, 2001

Related U.S. Application Data

(63) Continuation-in-part of application No. 09/750,595, filed on Dec. 28, 2000, which is a continuation-in-part of application No. 09/750,655, filed on Dec. 28, 2000, now Pat. No. 6,759,054, which is a continuation-in-part of application No. 09/621,123, filed on Jul. 21, 2000, now Pat. No. 6,503,944, which is a continuation-in-part of application No. 09/540, 242, filed on Mar. 31, 2000, now abandoned.

(51) Int. Cl.[7] ........................... B05D 1/40; A61L 27/00

(52) U.S. Cl. ...................... 427/2.24; 427/2.1; 427/2.25; 427/346; 427/420; 427/421; 427/425; 427/446; 427/447; 514/772.2; 623/1.15

(58) Field of Search ................................ 427/2.1, 2.24, 427/2.25, 446, 447, 420, 421, 346, 425; 514/772.2; 623/1.15

(56) References Cited

U.S. PATENT DOCUMENTS

| | | | | | |
|---|---|---|---|---|---|
| 2,072,303 | A | | 3/1937 | Herrmann et al. | 128/335.5 |
| 4,269,713 | A | * | 5/1981 | Yamashita et al. | 210/500.23 |
| 4,733,665 | A | | 3/1988 | Palmaz | 128/343 |
| 4,800,882 | A | | 1/1989 | Gianturco | 128/343 |
| 4,839,055 | A | * | 6/1989 | Ishizaki et al. | 210/641 |
| 4,886,062 | A | | 12/1989 | Wiktor | 128/343 |
| 4,977,901 | A | | 12/1990 | Ofstead | 128/772 |
| 5,328,471 | A | | 7/1994 | Slepian | 604/101 |
| 5,464,650 | A | | 11/1995 | Berg et al. | 427/2.3 |
| 5,578,073 | A | | 11/1996 | Haimovich et al. | 623/1 |
| 5,605,696 | A | | 2/1997 | Eury et al. | 424/423 |
| 5,628,730 | A | | 5/1997 | Shapland et al. | 604/21 |
| 5,667,767 | A | | 9/1997 | Greff et al. | 424/9.411 |
| 5,670,558 | A | | 9/1997 | Onishi et al. | 523/112 |
| 5,700,286 | A | | 12/1997 | Tartaglia et al. | 623/1 |
| 5,716,981 | A | | 2/1998 | Hunter et al. | 514/449 |
| 5,800,392 | A | | 9/1998 | Racchini | 604/96 |
| 5,824,049 | A | | 10/1998 | Ragheb et al. | 623/1 |
| 5,830,178 | A | | 11/1998 | Jones et al. | 604/49 |
| 5,837,313 | A | | 11/1998 | Ding et al. | 427/2.21 |
| 5,851,508 | A | | 12/1998 | Greff et al. | 424/9.411 |
| 5,865,814 | A | | 2/1999 | Tuch | 604/265 |
| 5,873,904 | A | | 2/1999 | Ragheb et al. | 623/1 |
| 5,971,954 | A | | 10/1999 | Conway et al. | 604/96 |
| 5,980,928 | A | | 11/1999 | Terry | 424/427 |
| 5,980,972 | A | | 11/1999 | Ding | 427/2.24 |
| 6,010,530 | A | | 1/2000 | Goicoechea | 623/1 |
| 6,015,541 | A | | 1/2000 | Greff et al. | 424/1.25 |
| 6,096,070 | A | | 8/2000 | Ragheb et al. | 623/1 |
| 6,153,252 | A | | 11/2000 | Hossainy et al. | 427/2.3 |
| 6,165,212 | A | | 12/2000 | Dereume et al. | 623/1.13 |
| 6,368,658 | B1 | * | 4/2002 | Schwarz et al. | 427/2.15 |
| 6,503,954 | B1 | * | 1/2003 | Bhat et al. | 514/772.2 |
| 6,555,157 | B1 | * | 4/2003 | Hossainy | 427/2.24 |

FOREIGN PATENT DOCUMENTS

| | | |
|---|---|---|
| EP | 0 665 023 | 8/1995 |
| EP | 0 970 711 | 1/2000 |
| WO | WO 91/12846 | 9/1991 |
| WO | WO 97/45105 | 12/1997 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 | 1/2001 |
| WO | WO 01/45763 | 6/2001 |

OTHER PUBLICATIONS

Barath et al., *Low Dose of Antitumor Agents Prevents Smooth Muscle Cell Proliferation After Endothelial Injury*; JACC vol. 13, No. 2; Feb. 1989:252A (Abstract).

Dichek et al., *Seeding of Intravascular Stents With Genetically Engineered Endothelial Cells*, Circulation 1989; 1347–1353.

Forrester et al., *A Paradigm for Restenosis Based on Cell Biology: Clues for the Development of New Preventive Therapies*, J. Am. Coll. Cardio. 1991; 17:758–769.

Matsumaru et al., *Embolic Materials For Endovascular Treatment of Cerebral Lesions*; J. Biomater. Sci. Polymer Edn, vol. 8, No. 7 (1997), pp. 555–569.

Miyazaki et al., *Antitumor Effect of Implanted Ethylene–Vinyl Alcohol Copolymer Matrices Containing Anticancer Agents on Ehrlich Ascites Carcinoma and P388 Leukemia in Mice*, Chem. Pharm. Bull. 33(6) (1985), pp. 2490–2498.

Miyazawa et al., *Effects of Pemirolast and Tranilast on Intimal Thickening After Arterial Injury in the Rat*; J. Cardiovasc. Pharmacol. (1997), pp. 157–162.

Ohsawa et al., *Preventive Effects of an Antiallergic Drug, Pemirolast Potassium, on Restenosis After Percutaneous Transluminal Coronary Angioplasty*; American Heart Journal (1998); pp. 1081–1087.

Shigeno, *Prevention of Cerebrovacular Spasm by Bosentan, Novel Endothelin Receptor*; Chemical Abstract 125:212307 (1996).

* cited by examiner

*Primary Examiner*—Judy M. Reddick
(74) *Attorney, Agent, or Firm*—Cameron K. Kerrigan; Squire, Sanders & Dempsey

(57) ABSTRACT

A composition comprising an ethylene vinyl alcohol copolymer and a dimethyl acetamide solvent is provided for forming a coating on prostheses such as stents. The composition can include an active agent or therapeutic substance. Methods are also provided for coating the stents.

19 Claims, 6 Drawing Sheets

ETHYLENE VINYL ALCOHOL-DIMETHYL ACETAMIDE COMPOSITION AND A METHOD OF COATING A STENT

CROSS-REFERENCE

This is a continuation-in-part of application Ser. No. 09/750,595 filed on Dec. 28, 2000; this application is also a continuation-in-part of application Ser. No. 09/750,655 filed on Dec. 28, 2000, now U.S. Pat. No. 6,759,054 which is a continuation-in-part of application Ser. No. 09/621,123 filed on Jul. 21, 2000, now U.S. Pat. No. 6,503,944 which is a continuation-in-part of application Ser. No. 09/540,242 filed on Mar. 31, 2000 (now abandoned).

BACKGROUND OF THE INVENTION

This invention relates to compositions for coating an implantable device or an endoluminal prosthesis, such as a stent. Moreover, the invention is directed to methods of coating a stent. The invention also relates to a biocompatible carrier containing an active agent for sustained release of the active agent to certain target cell populations, such as smooth muscle cells, requiring modulation to ameliorate a diseased state, particularly for the treatment of stenosis or restenosis following a vascular trauma or disease.

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Vasospasms and recoil of the vessel wall also threaten vessel closure. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in patent literature disclosing stents which have been successfully applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor. Mechanical intervention via stents has reduced the rate of restenosis as compared to balloon angioplasty; restenosis, however, is still a significant clinical problem. When restenosis does occur in the stented segment, its treatment can be challenging, as clinical options are more limited as compared to lesions that were treated solely with a balloon.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

SUMMARY OF THE INVENTION

A composition for coating a prosthesis such as a stent is provided. The composition comprises an amount of ethylene vinyl alcohol copolymer added to an amount of dimethyl acetamide solvent. The stent can be a radially expandable stent and can have a metallic body. The copolymer can constitute from about 0.1% to about 35% by weight of the total weight of the composition and the solvent can constitute from about 65% to about 99.9% by weight of the total weight of the composition.

In accordance with another embodiment, the composition can include an active agent such as actinomycin D, paclitaxel, docetaxel, or rapamycin. In this embodiment the copolymer can constitute about 0.1% to about 35%, the solvent about 50% to about 99.8%, and the active agent about 0.1% to about 40% by weight of the total weight of the composition.

In accordance with another embodiment, a co-solvent or a fluid can be added for increasing the dissolution of the active agent in the composition or for adjusting the wetting characteristic of the composition. The active agent can be added to the co-solvent prior to admixture with the composition. Suitable examples of the co-solvent can include, but are not limited to, propylene glycol methyl ether (PM), iso-propyl alcohol (IPA), n-propyl alcohol, methanol, ethanol, tetrahydrofuran (THF), dimethylformamide (DMF), and mixtures thereof.

In accordance with another aspect of the invention; a method of forming a composition to be applied to a stent is provided. The method comprises adding an amount of ethylene vinyl alcohol to an amount of dimethyl acetamide to form a composition used to form a coating for a stent. An active agent can also be added to the composition.

In accordance with another aspect of the invention, a method of coating a stent is provided comprising applying a composition to the stent; and blowing air onto the stent. The composition can include a polymer, such as ethylene vinyl alcohol copolymer, dissolved in a solvent, such as dimethyl acetamide. The composition can also include an active agent. The act of applying can be conducted by spraying the compositionat a flow rate of about 0.01 mg/second to about 1.0 mg/second. In accordance with one embodiment, the act of applying and blowing constitute a single cycle of coating application such that the method additionally includes repeating the cycle to form a coating of desirable weight or thickness. The act of applying the composition in a single cycle can be conducted from about 1 second to about 10 seconds. The act of blowing air in a single cycle can be conducted from about 3 seconds to about 60 seconds. About 0.1 micrograms to about 10 micrograms per cm of stent surface of coating can be deposited for each cycle. The blowing can be conducted at a temperature of about 30° C. to about 60° C. and at a flow rate of about 20 cubic feet/minute to about 80 cubic feet/minute. During the processing of the coating, the stent can be in an at least partially expanded state.

DETAILED DESCRIPTION OF THE EMBODIMENTS

Embodiments of the Composition

Figure 1A:
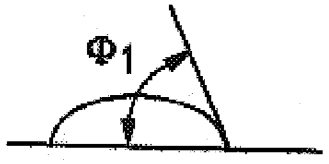
FIG. 1A illustrates a fluid on a solid substrate having a contact angle $\Phi_1$.

The embodiments of the composition are prepared by conventional methods wherein all components are combined, then blended. More particularly, in accordance to one embodiment, a predetermined amount of an ethylene vinyl alcohol copolymer (commonly known by the generic name EVOH or by the trade name EVAL) is added to a predetermined amount of dimethyl acetamide (DMAC or DMAc). If necessary, heating, stirring and/or mixing can be employed to effect dissolution of the copolymer into the solvent—for example in an 80° C. water bath for one to two hours.

Ethylene vinyl alcohol copolymer refers to copolymers comprising both ethylene and vinyl alcohol blocks. One of ordinary skill in the art understands that an ethylene vinyl alcohol copolymer may also be a terpolymer so as to include small amounts of additional monomers, for example less than about five (5) mole percentage of styrenes, propylene, or other suitable monomers. By way of example, the copolymer can comprise a mole percent of ethylene of from about 27% to about 48%. Ethylene vinyl alcohol copolymers are available commercially from companies such as Noltex LLC, La Porte, Tex., Aldrich Chemical Company, Milwaukee, Wis., Polyscience, Warrington, Pa., or EVAL Company of America, Lisle, Ill., or can be prepared by conventional polymerization procedures that are well known to one of ordinary skill in the art.

Synonyms of dimethyl acetamide (DMAC) include N,N,-dimethylacetamide, dimethylamide, acetdimethylamide, dimethylamide acetate, and acetyldimethylamine. Properties of DMAC are illustrated in Table 1:

TABLE 1

| Formula | Mol. Weight | Dielectric Constant ϵ | Boiling Point ° C. @ 1 atm. | Vapor Pressure, torr, at 25° C. | Density | Reflective Index | Surface Tension Dyne/cm | Viscosity Centipoise @ 20° C. |
|---|---|---|---|---|---|---|---|---|
| $C_4H_9NO$ | 87.12 | 37.78 | 166.1 | 1.3 | 0.937 | 1.421 | 32.43 | 2.14 |

Superior and unexpected results have been discovered with the use of ethylene vinyl alcohol as a coating for a stent and DMAC as the platform for the solvent system. The copolymer illustrated tenacious adhesive qualities to metallic surfaces, particularly stainless steel; provides a non-brittle coating; and does not significantly recoil subsequent to the expansion of the copolymer. DMAC is capable of placing most grades of ethylene vinyl alcohol copolymers into dissolution. As indicated by Table 1, DMAC harbors a high vapor pressure, as compared to conventional solvent systems, which allows not only for DMAC to evaporate more rapidly, but also for lower processing temperatures for the formation of the coating onto the device. Processing temperatures as low as, for example, ambient temperature to about 50° C. can be employed. A low processing temperature is advantageous in that most therapeutic or active agents, such as actinomycin D, react adversely to heat, more particularly when combined with a solvent system. DMAC is also a stable platform for most therapeutic substances. The solvent serves as a more compatible or benign solution as it does not adversely react with or propagate the degradation of therapeutic or active agents. Additionally advantageous characteristics of DMAC include low solution viscosity and surface tension and a desirable "wetting" property. It has been unexpectedly discovered that the use of DMAC resulted in a more uniform application of the copolymer onto the surface of the device; significantly reduced defects such as "cob webs" or "pool webs" of the polymer interconnected between the stent struts; prevented conglomeration of coating clumps leading to an uneven coating profile; and provided for smoother coating surface. Examples were conducted coating a stent with up to 800 micrograms of the copolymer with minimum coating defects.

Figure 1B:
FIG. 1B illustrates a fluid on a solid substrate having a contact angle $\Phi_2$.
Figure 2A:
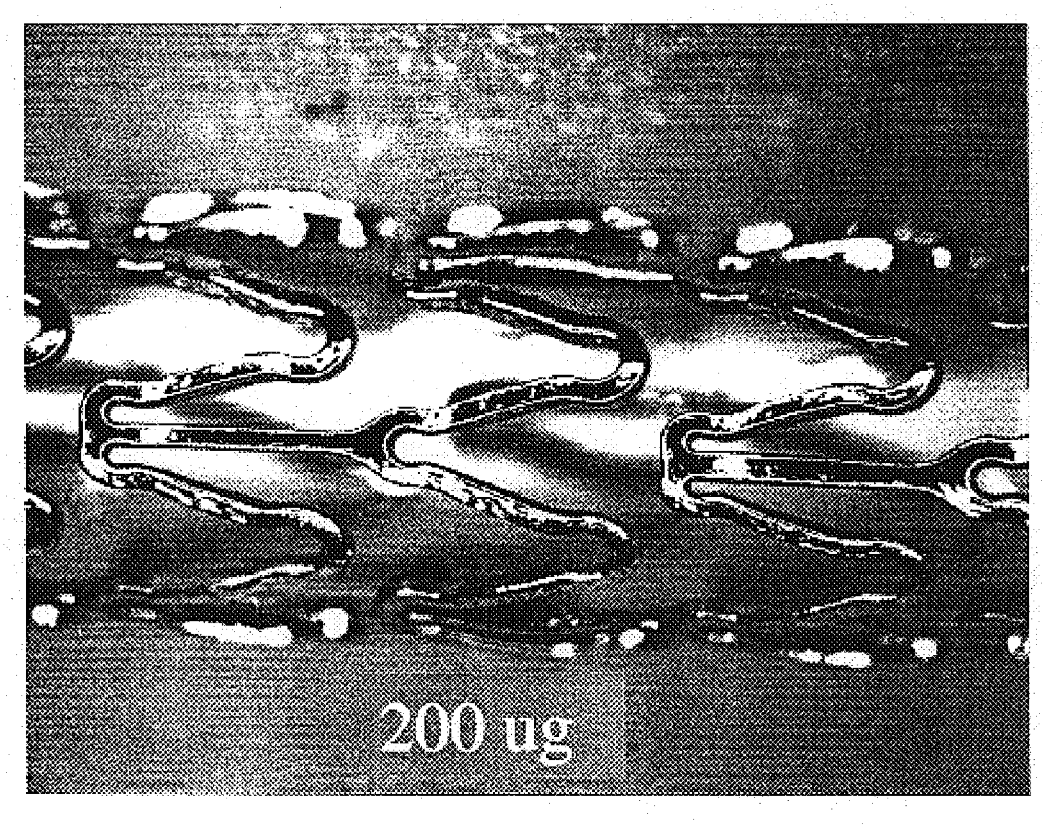
FIGS. 2A-2D are photographs of stents coated with a composition of the present invention.
Figure 2B:
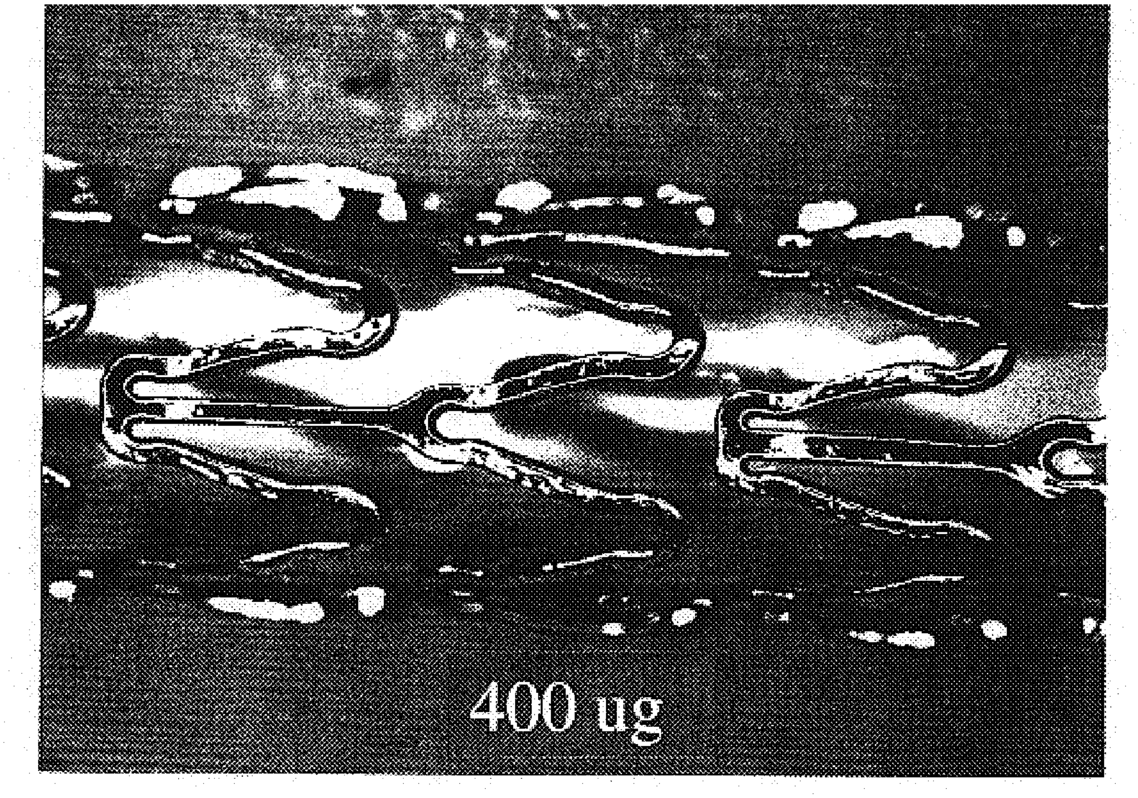
Figure 2C:
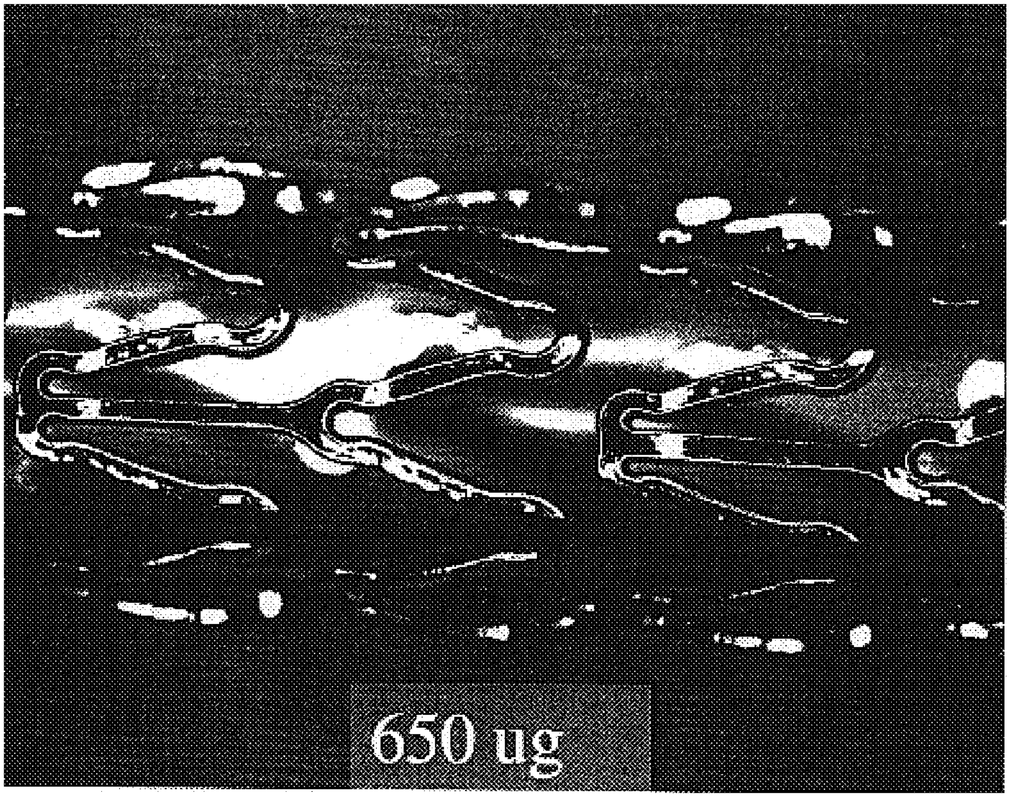
Figure 2D:
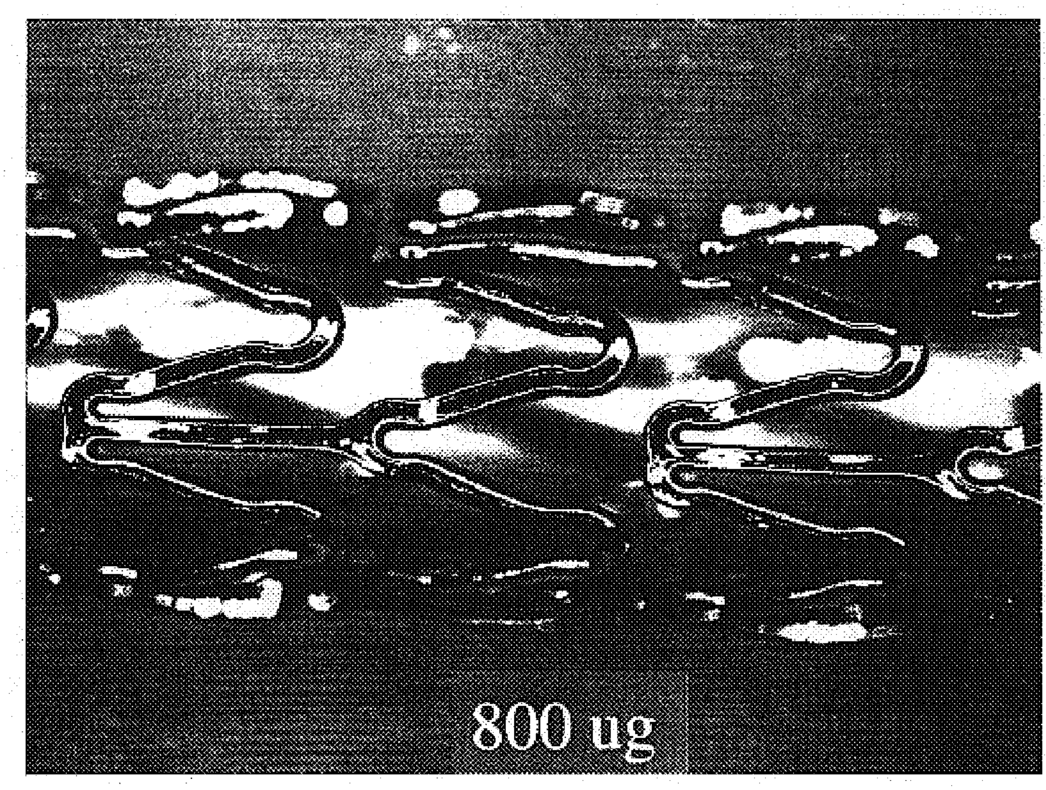

"Wetting" is defined by capillary permeation. Capillary permeation is the movement of a fluid on a solid substrate driven by interfacial energetics, Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. FIG. 1A illustrates a fluid droplet on a solid substrate, for example a stainless steel surface. Fluid droplet has a high capillary permeation that corresponds to a contact angle $\Phi_1$, which is less than about 90°. In contrast, FIG. 1B illustrates a fluid droplet on solid substrate having a low capillary permeation that corresponds to a contact angle $\Phi_2$, which is greater than about 90°.

By way of example, the ethylene vinyl alcohol copolymer can comprise from about 0.1% to about 35%, more narrowly from about 1% to about 10% by weight of the total weight of the composition; and the solvent can comprise from about 65% to about 99.9%, more narrowly from about 90% to about 99% by weight of the total weight of the composition. A specific weight ratio is dependent on factors such as the material from which the prosthesis. is made, the geometrical structure of the prosthesis, and the coating application technique employed.

Active Agent

In accordance with another embodiment, sufficient amounts of an active agent or therapeutic substance for causing preventative or therapeutic effects can be dispersed in the blended composition of the ethylene vinyl alcohol copolymer and the DMAC solvent. As a general rule, an increase in the amount of the ethylene comonomer content decreases the rate that the active agent is released from the copolymer matrix. The release rate of the active agent typically decreases as the hydrophilicity of the copolymer decreases. An increase in the amount of the ethylene content increases the overall hydrophobicity of the copolymer, especially as the content of vinyl alcohol is concomitantly reduced.

In this embodiment, by way of example, the ethylene vinyl alcohol copolymer can comprise from about 0.1% to about 35%, more narrowly from about 1% to about 10% by weight of the total weight of the composition; the DMAC solvent can comprise from about 50% to about 99.8%, more narrowly from about 85% to about 98.9% by weight of the total weight of the composition; and the active agent can comprise from about 0.1% to about 40%, more narrowly from about 0.1% to about 5% by weight of the total weight of the composition. Selection of a specific weight ratio of the ethylene vinyl alcohol copolymer and the solvent is dependent on factors such as the material from which the device is made, the geometrical structure of the device, the type and amount of the active agent employed, and the coating application technique employed.

In accordance with another embodiment, a second solvent or a fluid can be used to improve the solubility of the active agent in the composition or to adjust the wetting of the compostion. Accordingly, higher active agent concentrations can be formulated. Sufficient amounts of a second solvent such as propylene glycol methyl ether (PM), iso-propyl alcohol (IPA), n-propyl alcohol, methanol, ethanol, tetrahydrofuran (THF), dimethylformamide (DMF), and mixtures thereof, can be added to the blended composition. Alternatively, the active agent can be added to the second solvent prior to admixture with the composition.

The particular weight percentage of the active agent mixed within the composition, with or without the second solvent, depends on factors such as duration of the release, cumulative amount of release, and release rate that is desired. It is known that the release rate and the cumulative amount of the active agent that is released are directly proportional to the total initial content of the agent in the copolymer matrix. Accordingly, a wide spectrum of release rates can be achieved by modifying the ethylene content and the initial amount of the active agent.

The active agent should be in true solution or saturated in the blended composition. If the active agent is not completely soluble in the composition, operations including mixing, stirring, and/or agitation can be employed to effect homogeneity of the residues. The active agent may be added in fine particles. The mixing of the active agent can be conducted at ambient pressure and at room temperature such that supersaturating the active ingredient is not desired. The active agent could be for inhibiting the activity of vascular smooth muscle cells. More specifically, the active agent can be aimed at inhibiting abnormal or inappropriate migration and/or proliferation of smooth muscle cells. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, and antioxidant substances. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck), calcium channel blockers (such as Nifedipine), coichicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, rapamycin, and dexamethasone.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Implantable Devices or Prostheses

In accordance with the above-described method, the active agent can be applied to an implantable device or prosthesis, e.g., a stent, retained on the stent during delivery and expansion of the stent, and released at a desired control rate and for a predetermined duration of time at the site of implantation. The release rate of the active agent can be controlled by modifying release parameters such as the amount of ethylene comonomer content of the copolymer and the initial active ingredient content in the matrices of the copolymer. The rate of release can also be adjusted by the addition of a diffusion barrier layer. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Methods for Coating

To form a coating on a surface of the implantable device or prosthesis, the surface of the device should be clean and free from contaminants that may be introduced during manufacturing. However, the surface of the device requires no particular surface treatment to retain the applied coating. The composition can be applied to both the inner and outer (the tissue contacting) surfaces of the device. Application of the composition can be by any conventional method, such as by spraying the composition onto the device or immersing the device in the composition.

By way of illustration, a spray apparatus, such as EFD 780S spray device with VALVEMATE 7040 control system (manufactured by EFD Inc., East Providence, R.I.) can be used to apply the composition to the stent. EFD spray device is an air-assisted external mixing atomizer. The composition is atomized into small droplets by air and uniformly applied to the stent surface. The atomization pressure can be maintained at a range of about 5 to 20 psi. The droplet size depends on such factors as viscosity of the solution, surface tension of the solvent, and atomizing pressure. Other types of spray applicators, including air-assisted internal mixing atomizers and ultrasonic applicators can also be used for the application of the composition.

During the application of the composition, the stent can be rotated about the stent's central longitudinal axis. Rotation of the stent can be from about 1 rpm to about 300 rpm, more narrowly about 50 rpm to about 150 rpm. By way of example, the stent can rotate at about 120 rpm. The stent can also be a moved in a linear direction along the same axis. The stent can be moved at about 1 mm/sec. to about 12 mm/sec., for example about 6 mm/sec. or for a minimum of at least two passes (i.e., back and forth passed the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition is about 1 second to about 10 seconds, for example about 5 seconds, in duration. The amount of coating applied by each repetition can be about 0.1 micrograms/cm (of stent surface) to about 10 micrograms/cm, for example less than about 2 micrograms/cm per 5 second spray.

Each repetition can be followed by removal of a significant amount of the solvent(s) by application of warm air. The application of warm air between each repetition prevents coating defects and minimizes interaction between the active agent and the solvent. The temperature of the warm air can be about 30° C. to about 60° C., more narrowly about 40° C. to about 50° C. The flow rate of the warm air can be from about 20 cubic feet/minute (CFM) (0.57 cubic meters/minute(CMM)) to about 80 CFM (2.27 CMM), more narrowly about 30 CFM (0.85 CMM) to about 40 CFM (1.13 CMM). The warn air can be applied for about 3 seconds to about 60 seconds, more narrowly about 10 seconds to about 20 seconds. Applications can be performed at a temperature of about 50° C., the flow rate of about 40 CFM, and for about 10 seconds. Any suitable number of sets of application of the composition followed by blowing of warm air can be performed to form a coating of a desired thickness or weight. Excessive application of the polymer can, however, cause coating defects.

Operation such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off the surface of the device.

In accordance with one embodiment, the stent can be least partially pre-expanded prior to the application of the composition. For example, the stent can be radially expanded about 20% to about 60%, more narrowly about 27% to about 55%—the measurement being taken from the stent's inner diameter at an unexpanded position to the inner diameter at the expanded position. The expansion of the stent, for increasing the interspace between the stent struts, during the application of the composition, can further prevent "cob web" or "pool web" formation between the stent struts.

To form an optional primer layer on the surface of the device, an embodiment of the composition free from any active agents is applied to the surface of the device. For the primer layer, the composition could be exposed to a heat treatment at a temperature range of greater than about the glass transition temperature and less than about the melting temperature of the copolymer. The device should be exposed to the heat treatment for any suitable duration of time (e.g., 30 minutes) which would allow for the formation of the primer layer on the surface of the device and allows for the evaporation of the solvent. The primer can be used for increasing the retention of a reservoir coating containing the active agent on the surface of the device, particularly metallic surfaces such as stainless steel. The primer can act as an intermediary adhesive tie layer between the surface of the device and the coating carrying the active agent—which, in effect, allows for the quantity of the active agent to be increased in the reservoir coating.

For the formation of the reservoir coating containing an active agent, an embodiment of the composition containing an active agent or combination of agents is applied to the device. If a primer layer is employed, the application should be performed subsequent to the drying of the primer layer. The DMAC solvent or the combination of the DMAC solvent and second solvent is removed from the composition applied to the surfaces of the device by allowing the solvent or combination of the solvents to evaporate. Heating the device at a predetermined temperature for a predetermined period of time can induce evaporation.

An optional diffusion barrier can be formed over the reservoir coating containing the active agents. An embodiment of the composition, free from any active agents, can be applied to a selected portion of the reservoir region subsequent to the drying of the reservoir region. The solvent is then allowed to evaporate, for example, by exposure to a selected temperature, to form the rate-limiting diffusion barrier.

For the reservoir coating containing the active agent and the optional diffusion barrier, a final heat treatment could be conducted to remove essentially all of the solvent(s). The heat treatment can be conducted at about 30° C. to about 60° C. for about 15 minutes to no longer than 4 hours. Higher degrees of temperature may adversely affect the characteristics of the active agent. The heating can be conducted in an anhydrous atmosphere and at ambient pressure. The heating can, alternatively, be conducted under a vacuum condition. It is understood that essentially all of the solvent(s) will be removed from the composition but traces or residues can remain blended with the copolymer.

Coating Layers

The ethylene vinyl alcohol copolymer is a biocompatible coating, i.e., a coating which, in the amounts employed, is non-toxic, non-inflammatory, chemically inert, and substantially non-immunogenetic. The copolymer also includes a high percentage of an —OH functional group which is susceptible to attachment of active agents as well as further surface modification—such as specific interaction with a secondary —OH functional group. The inclusion of the active agent in the copolymer matrix allows for not only the retention of the active agent on the stent during delivery and, if applicable, expansion of the stent, but also the controlled and sustained administration of the active agent following implantation. By way of example, and not limitation, the impregnated ethylene vinyl alcohol copolymer reservoir coating can have a thickness of about 0.5 microns to about 10 microns. The particular thickness of reservoir coating is based on the type of procedure for which prosthesis is employed and the amount of the active agent that is desired to be delivered. Applying a plurality of reservoir coating layers onto the prosthesis can further increase the amount of the active ingredient to be carried by the prosthesis, without causing coating defects.

As for an optional primer layer, ethylene vinyl alcohol copolymer adheres very well to metallic surfaces, particularly stainless steel. Accordingly, the copolymer, free from any active agents, provides for a strong adhesive tie between the reservoir coating and the surface of the stent. By way of example and not limitation, the optional primer layer can have a thickness of about 0.1 microns to about 2 microns.

The diffusion barrier layer can also be made from any other suitable biocompatible materials. Examples of such polymeric materials include silicones, fluoro-polymers, poly (L-lactic acid), polycaprolactone, poly(hyrodxyvalerate), polyolefins, polyurethanes, polyisobutylene, and other biostable or bioabsorbable polymers. The diffusion barrier can have a thickness of about 0.2 microns to about 10 microns. It is understood by one of ordinary skill in the art that the thickness of the diffusion barrier is based on factors such as the type stent, type of procedure for which the stent is employed and the rate of release that is desired.

Method of Use

In accordance with the above-described method, the active agent can be applied to an implantable device or prosthesis, e.g., a stent, retained on the stent during delivery and expansion of the stent, and released at a desired control rate and for a predetermined duration of time at the site of implantation. The release rate of the active agent can be controlled by modifying release parameters such as the amount of ethylene comonomer content of the copolymer and the initial active ingredient content in the matrices of the copolymer. The rate of release can also be adjusted by the addition of a diffusion barrier layer. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating may then be expanded at the desired area of treatment. A post insertion angiogram may also be utilized to confirm appropriate positioning.

EXAMPLES

The embodiments of the invention will be illustrated by the following set forth examples which are being given by way of illustration only and not by way of limitation. All parameters and data are not be construed to unduly limit the scope of the embodiments of the invention.

Example 1

Coating Procedure for Depositing EVAL Primer on a 13 mm Multi-Link Tetra™ Stent Using a Translational Coater A Multi-Link Tetra™ stent (available from Guidant Corporation) was placed over a tapered mandrel and expanded from an unexpanded inner diameter of 1.473 mm (0.058 inches) to the inner diameter of 1.778 mm (0.074 inches). The expanded stent was cleaned by placement in an ultrasonic bath of isopropyl alcohol solution for 15 minutes. The stent was dried and plasma cleaned in a plasma chamber. A 2% by weight of EVOH solution was made with DMAC. The solution was transferred to a barrel attached to an EFD spray nozzle. The composition was deposited onto the stent to form the primer layer by atomizing the solution into fine droplets. The atomization pressure was maintained at about 10 to 15 psi. The rotational speed was at 120 rpm. The stent was passed under the EFD spray nozzle for about ten seconds. The stent was advanced from a first point to a second point (distance of about 25 mm) at a translational speed of about 6 mm per second and was withdrawn from the second point back to the first point at the same speed. The stent was moved to the warm air drying station for removing most of the solvent. The deposit weight per cycle was controlled at 10 μg. The process was repeated to deposit five layers. The primered stent was allowed to dry for about 60 minutes at a temperature of about 140° C.

Example 2

Coating Procedure for Depositing Actinomycin-D on a 13 mm Multi-Link Tetra™ Stent Using a Translational Coater A primered Multi-Link Tetra™ stent formed as per Example 1 was placed over a spray mandrel. The mandrel was designed to provide support at the edges of the stent during rotation. An actinomycin D/EVOH solution was made with 0.2 grams of EVOH, 0.067 grams of actinomycin D, and 9.733 grams of DMAC solvent, making EVOH:actinomycin D ratio of 3 to 1. The solution was transferred to the barrel for the EFD spray nozzle. The composition was sprayed onto the stent. The atomization pressure was maintained at about 10 to 15 psi. The rotational speed was maintained at 120 rpm. The stent was passed under the EFD spray nozzle for about ten seconds. The stent was advanced from the first point to the second point at a translational speed of about 6 mm per second, and was withdrawn from the second point back to the first point at the same speed. The stent was then moved to the warm air drying station for removing most of the solvent. The deposit weight per cycle was controlled at 10 μg. The process was repeated to deposit 500 micrograms of coating. The drug-coated stent was allowed to dry in an oven for about 120 minutes at a temperature of about 50° C.

Example 3

Coating Procedure for Depositing EVOH Overcoat as the Rate-Limiting Layer on a 13 mm Multi-Link Tetra™ Stent Using a Translational Coater A drug coated Multi-Link Tetra™ stent formed as per Example 2 was placed over a spray mandrel. An EVOH solution was made with 0.2 grams of EVOH and 9.8 grams of a DMAC solvent. The solution was transferred to the barrel attached to the EFD spray nozzle. The composition was applied to the stent to form the barrier layer. The atomization pressure was maintained at 10 to 15 psi. The translational speed was set at 6 mm per second and the rotational speed was set at 120 rpm. The stent was passed under the EFD spray nozzle for about ten seconds. The stent was moved to the warm air drying station for removing most of the solvent. The deposit weight per cycle was controlled at 10 micrograms. The process was repeated to deposit 400 micrograms of coating. The drug-coated stent was allowed to dry for about 120 minutes at a temperature of about 50° C.

Example 4

Coating Procedure for Depositing EVAL Coating on a 13 mm Multi-Link Tetra™ Stent Using a Translational Coater A Multi-Link Tetra™ stent was place over a tapered mandrel and extended from an unexpanded inner diameter of 1.473 mm (0.058 inches) to the inner diameter of 1.879 mm (0.074 inches). The expanded stent was then cleaned by placement in an ultrasonic bath of isopropyl alcohol solution for 15 minutes. The stent was dried and plasma cleaned in a plasma chamber. A 2% by weight of EVOH solution was made with DMAC. The solution was transferred to the barrel attached to an EFD spray nozzle. The composition was deposited onto the stent to form the primer layer. The atomization pressure was maintained at about 10 to 15 psi. The translational speed was set at 6 mm per second and the rotational speed was kept at 120 rpm. The stent was passed under the EFD spray nozzle for about ten seconds. The stent was advanced from the first point to the second point and was returned from the second point back to the first point at the same speed. The stent was moved to the warm air drying station for removing most of the solvent. The deposit weight per cycle was control at 10 μg. The process was repeated to deposit four layers. The primered stent was allowed to dry for about 60 minutes at a temperature of about 140° C. After the drying step, the primered stent was placed on a spray mandrel and then passed under the EFD spray nozzle for about ten seconds. The stent was again moved to the warm air drying station for removing most of the solvent. The deposit weight per cycle was controlled at 10 μg. The process was repeated to deposit 800 micrograms of EVAL coating. The drug-coated stent was allowed to dry in an oven for about 120 minutes at a temperature of about 50° C.

Example 5

FIGS. 2A, 2B, 2C, and 2D are photographs illustrating EVAL coated stent including 200 μg, 400 μg, 650 μg, and 800 μg coating, respectively. The coatings illustrate smooth coating finish, minimal coating defects, and superior coating uniformity.

Example 6

Release Profile of Actinomycin D From EVAL Coated Stents in Water

Figure 3A:
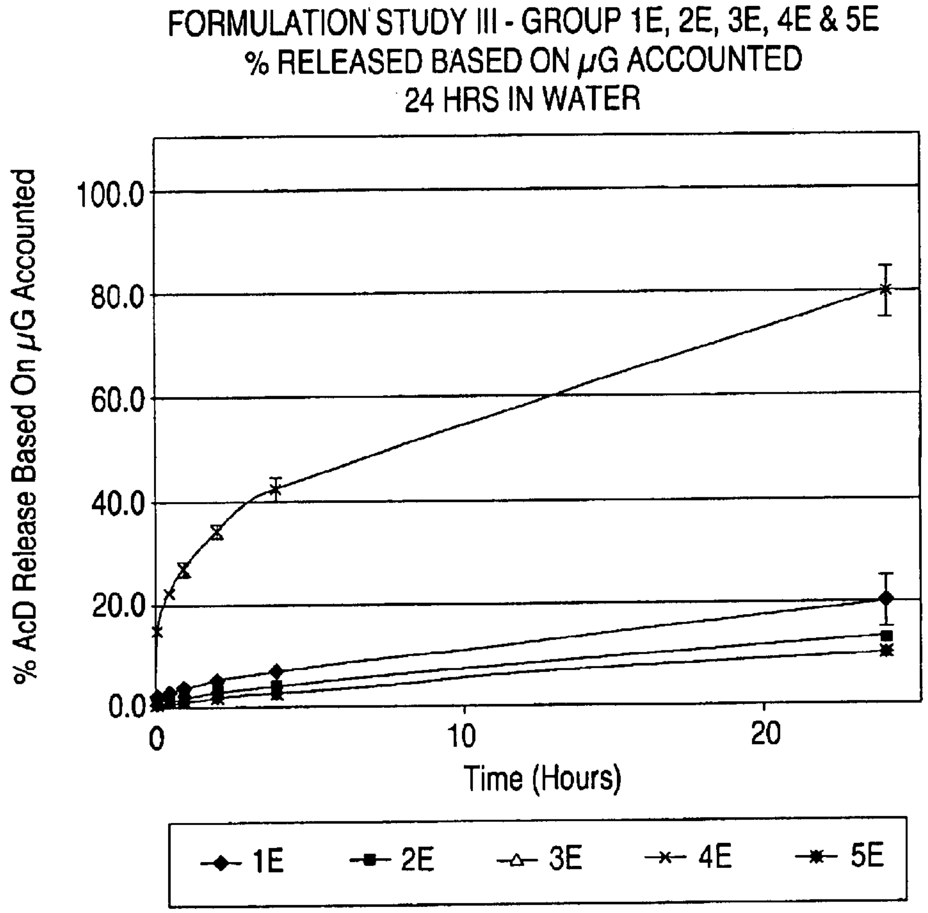
FIGS. 3A and 3B are graphs illustrating the release rate of actinomycin D in accordance with Example 6.
Figure 3B:
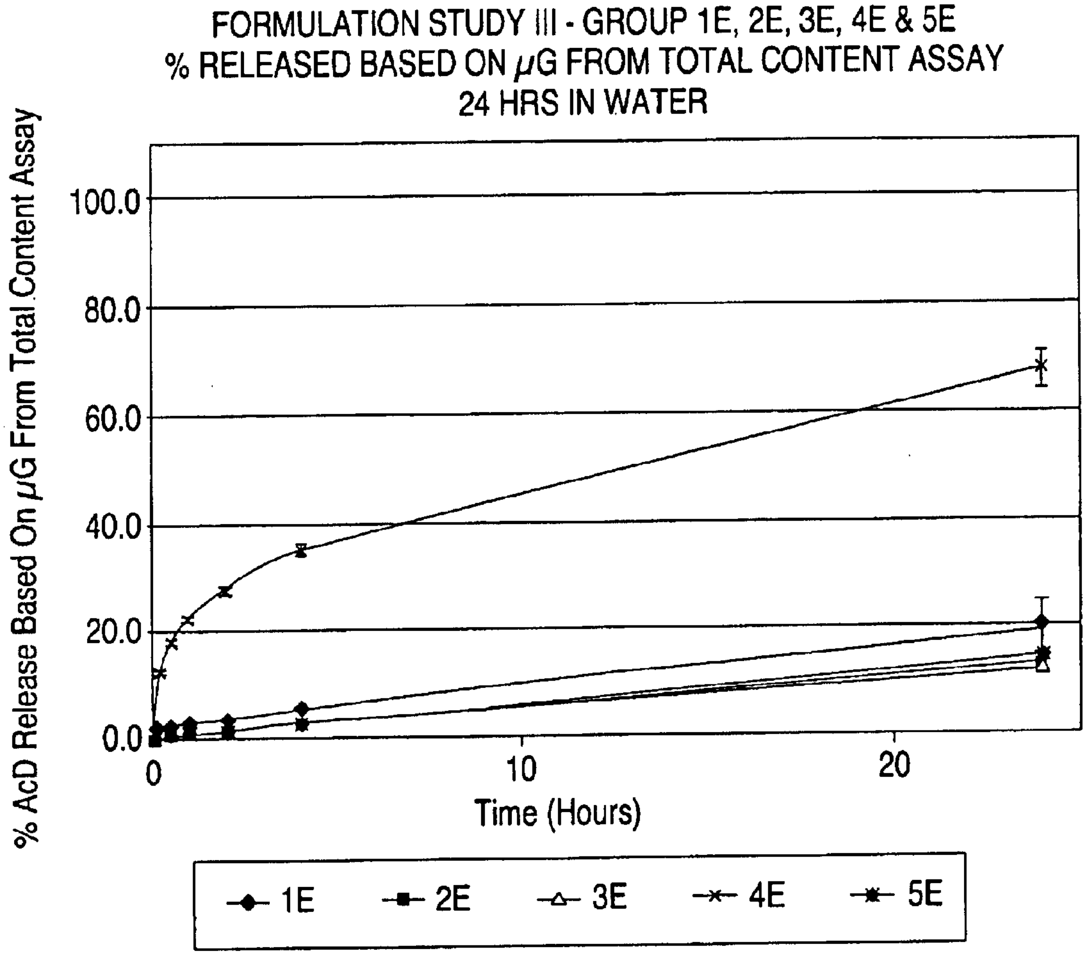

All groups formed with a DMAC solvent system. Reference is made to FIGS. 3A and 3B for the graphical depiction of the results.

Group 1E: 1:3 actinomycin D:EVAL composition for forming coating containing 50 μg of actinomycin D. 200 μg EVAL top coating formed for a diffusion layer.

Group 2E: 1:3 actinomycin D:EVAL composition for forming coating containing 50 μg of actinomycin D. 300 μg topcoat.

Group 3E: 1:3 actinomycin D:EVAL composition for forming coating containing 50 μg of actinomycin D. 400 μg topcoat.

Group 4E: 1:3 actinomycin D:EVAL composition for forming coating containing 50 μg of actinomycin D. No topcoat was formed.

Group 5E: 1:3 actinomycin D:EVAL composition for forming coating containing about 100 μg of actinomycin D. 200 μg topcoat.

| | 1E | | | | 2E | | | | 3E | | | | 4E | | | | 5E | | | |
|---|---|---|---|---|---|---|---|---|---|---|---|---|---|---|---|---|---|---|---|---|
| | Based on μg accounted % | | Based on μg from Total Content | | Based on μg accounted % | | Based on μg from Total Content | | Based on μg accounted % | | Based on ug from Total Content | | Based on ug accounted | | Based on μg from Total Content | | Based on ug accounted | | Based on μg from Total Content | |
| Time Hours | Release | SD | % Release | SD | Release | SD | % Release | SD | Release | SD | % Release | SD | % Release | SD | % Release | SD | % Release | SD | % | |
| 0 | 0.0 | 0.0 | 0.0 | 0.0 | 0.0 | 0.0 | 0.0 | 0.0 | 0.0 | 0.0 | 0.0 | 0/0 | 0.0 | 0.0 | 0.0 | 0.0 | 0.0 | 0.0 | 0.0 | 0.0 |
| 0.17 | 1.6 | 0.2 | 1.4 | 0.3 | 0.9 | 0.2 | 0.8 | 0.2 | 0.7 | 0.1 | 0.7 | 0.3 | 15.6 | 0.5 | 13.0 | 0.4 | 0.5 | 0.2 | 0.5 | 0.1 |
| 0.5 | 2.3 | 0.4 | 2.0 | 0.4 | 1.4 | 0.2 | 1.2 | 0.1 | 0.9 | 0.3 | 1.0 | 0.3 | 21.9 | 0.3 | 18.3 | 0.3 | 0.8 | 0.2 | 0.8 | 0.1 |
| 1 | 3.1 | 0.4 | 2.7 | 0.4 | 1.9 | 0.2 | 1.6 | 0.1 | 1.3 | 0.4 | 1.4 | 0.6 | 27.3 | 1.0 | 22.8 | 0.3 | 1.2 | 0.4 | 1.2 | 0.1 |
| 2 | 4.3 | 0.8 | 3.8 | 0.7 | 2.5 | 0.4 | 2.2 | 0.2 | 1.9 | 0.3 | 2.0 | 0.7 | 33.8 | 1.2 | 28.2 | 0.6 | 1.7 | 0.4 | 1.7 | 0.1 |
| 4 | 6.3 | 1.2 | 5.4 | 1.1 | 3.7 | 0.6 | 3.2 | 0.4 | 2.6 | 0.7 | 2.8 | 1.0 | 42.4 | 1.8 | 35.4 | 0.9 | 2.6 | 0.6 | 2.7 | 0.0 |
| 24 | 20.7 | 4.6 | 18.0 | 4.0 | 13.2 | 3.0 | 11.4 | 2.0 | 9.5 | 2.9 | 10.1 | 4.2 | 80.0 | 5.1 | 66.7 | 3.4 | 13.1 | 4.2 | 13.0 | 1.2 |
| <tract | 100.0 | 0.0 | 86.7 | 3.7 | 100.0 | 0.0 | 86.8 | 5.5 | 100.0 | 0.0 | 109.5 | 49.6 | 100.0 | 0.0 | 83.4 | 2.1 | 100.0 | 0.0 | 105.1 | 28.4 |

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of coating a stent, comprising:

(a) mounting a stent onto a support assembly;

(b) rotating the stent while mounted on the support assembly;

(c) spraying a composition onto the stent while the stent is mounted on the support assembly, the composition including a solvent; and (d) blowing air onto the stent subsequent to the termination of the spraying of the composition to induce evaporation of at least a portion of the solvent from the composition.

2. The method of claim 1, wherein the composition includes a polymer dissolved in the solvent.

3. The method of claim 1, wherein the composition includes a polymer dissolved in the solvent and an active agent added thereto.

4. The method of claim 3, wherein the active agent is actinomycin D, paclitaxel, docetaxel, or rapamycin.

5. The method of claim 1, wherein the composition is sprayed onto the stent at a flow rate of about 0.01 mg/sec. to about 1.0 mg/sec.

6. The method of claim 1, wherein spraying the composition and blowing air constitute a single cycle of coating application and wherein the method additionally comprises repeating the cycle at least twice to form a coating of desirable weight.

7. The method of claim 6, wherein spraying the composition for a single cycle is conducted from about 1 second to about 10 seconds.

8. The method of claim 6, wherein blowing air for a single cycle is conducted from about 3 seconds to about 60 seconds.

9. The method of claim 6, wherein about 0.1 micrograms to about 10 micrograms per cm of stent surface of coating is deposited onto the stent for each cycle.

10. The method of claim 1, wherein the temperature of the air is about 30° C. to about 60° C.

11. The method of claim 1, wherein blowing air is conducted at a flow rate of about 20 cubic feet/minute to about 80 cubic feet/minute.

12. The method of claim 1, wherein the stent is rotated at about 1 rpm to about 300 rpm.

13. The method of claim 1, additionally comprising moving the stent in a linear direction along the longitudinal axis of the stent.

14. The method of claim 1, wherein the stent is in at least a partially expanded position during the spraying of composition and the blowing of air.

15. The method of claim 1, wherein the stent is rotated at about 50 rpm to about 100 rpm.

16. The method of claim 1, wherein the temperature of the air is about 40° C. to about 50° C.

17. The method of claim 1, wherein blowing air is conducted at a flow rate of about 30 cubic feet/minute to about 40cubic feet/minute.

18. The method of claim 6, wherein blowing air for a single cycle is conducted from about 10 seconds to about 20 seconds.

19. A method of coating a stent, comprising:

(a) mounting a stent onto a support assembly;

(b) rotating the stent while mounted on the support assembly;

(c) spraying a composition onto the stent while the stent is mounted on the support assembly, the composition including a solvent; and (d) blowing air onto the stent subsequent to the termination of the spraying of the composition to induce evaporation of at least a portion of the solvent from the composition, wherein the temperature of the air is about 30° C. to about 60° C., the flow rate of the air is about 20 cubic feet/minute to about 80 cubic feet/minute, and the duration of the application of air is about 3 seconds to about 60 seconds.

* * * * *